US009247918B2

(12) United States Patent
Sharma et al.

(10) Patent No.: US 9,247,918 B2
(45) Date of Patent: *Feb. 2, 2016

(54) COMPUTATION OF HEMODYNAMIC QUANTITIES FROM ANGIOGRAPHIC DATA

(71) Applicant: Siemens Aktiengesellschaft, Munich (DE)

(72) Inventors: Puneet Sharma, Monmouth Junction, NJ (US); Xudong Zheng, Plainsboro, NJ (US); Ali Kamen, Skillman, NJ (US); Lucian Mihai Itu, Brasov (RO); Bogdan Georgescu, Plainsboro, NJ (US); Dorin Comaniciu, Princeton Junction, NJ (US); Thomas Redel, Poxdorf (DE); Saikiran Rapaka, Ewing, NJ (US); Viorel Mihalef, Keasbey, NJ (US); Jan Boese, Eckental (DE)

(73) Assignee: Siemens Aktiengesellschaft (DE)

(*) Notice: Subject to any disclaimer, the term of this patent is extended or adjusted under 35 U.S.C. 154(b) by 6 days.

This patent is subject to a terminal disclaimer.

(21) Appl. No.: 13/937,313

(22) Filed: Jul. 9, 2013

(65) Prior Publication Data

US 2014/0024932 A1 Jan. 23, 2014

Related U.S. Application Data

(60) Provisional application No. 61/669,325, filed on Jul. 9, 2012, provisional application No. 61/812,346, filed on Apr. 16, 2013.

(51) Int. Cl.
A61B 5/00 (2006.01)
A61B 6/00 (2006.01)
G06F 19/00 (2011.01)

(52) U.S. Cl.
CPC .......... *A61B 6/507* (2013.01); *A61B 6/481* (2013.01); *A61B 6/504* (2013.01); *A61B 6/5217* (2013.01); *G06F 19/3437* (2013.01)

(58) Field of Classification Search
CPC ...... A61B 6/507; A61B 6/504; A61B 6/5217; A61B 5/02028
USPC .................................................. 600/407, 431
See application file for complete search history.

(56) References Cited

U.S. PATENT DOCUMENTS

| 8,157,742 | B2 | 4/2012 | Taylor |
| 8,249,815 | B2 | 8/2012 | Taylor |
| 8,311,747 | B2 | 11/2012 | Taylor |
| 8,311,748 | B2 | 11/2012 | Taylor et al. |
| 8,311,750 | B2 | 11/2012 | Taylor |
| 8,315,812 | B2 | 11/2012 | Taylor |

(Continued)

OTHER PUBLICATIONS

T. Tak, "Ejection Fraction Derived by Noninvasive Modalities Versus Left Ventricular Angiographic Determination," Clinical Medicine & Research, vol. 3, pp. 61-62, 2005.

(Continued)

*Primary Examiner* — Jonathan Cwern

(57) ABSTRACT

Methods for computing hemodynamic quantities include: (a) acquiring angiography data from a patient; (b) calculating a flow and/or calculating a change in pressure in a blood vessel of the patient based on the angiography data; and (c) computing the hemodynamic quantity based on the flow and/or the change in pressure. Systems for computing hemodynamic quantities and computer readable storage media are described.

13 Claims, 7 Drawing Sheets

(56) References Cited

U.S. PATENT DOCUMENTS

| | | | |
|---|---|---|---|
| 8,315,813 B2 | 11/2012 | Taylor et al. | |
| 8,315,814 B2 | 11/2012 | Taylor et al. | |
| 8,321,150 B2 | 11/2012 | Taylor | |
| 8,386,188 B2 | 2/2013 | Taylor et al. | |
| 2006/0210478 A1* | 9/2006 | Weisskoff | 424/9.36 |
| 2012/0022843 A1 | 1/2012 | Ionasec et al. | |
| 2012/0059246 A1* | 3/2012 | Taylor | 600/419 |
| 2012/0072190 A1* | 3/2012 | Sharma et al. | 703/2 |
| 2013/0132054 A1 | 5/2013 | Sharma et al. | |

OTHER PUBLICATIONS

A. Neubauer et al., "Clinical Feasibility of a Fully Automated 3D Reconstruction of Rotational Coronary X-Ray Angiograms," Circ. Cardiovasc. Interv., pp. 71-79, 2010.

R.F. Wilson et al., "Effects of Adenosine on Human Coronary Arterial Circulation," Circulation, pp. 1595-1606, vol. 82, No. 5, 1990.

S. Molloi et al., "Regional Volumetric Coronary Blood Flow Measurement by Digital Angiography," Academic Radiology, vol. 11, No. 7, pp. 757-766, 2004.

J. C.H. Schuurbiers et al., "In Vivo Validation of CAAS QCA-3D Coronary Reconstruction Using Fusion of Angiography and Intravascular Ultrasound (ANGUS)," Catheterization and Cardiovascular Interventions, vol. 73, pp. 620-626, 2009.

L. Grinberg et al., "Modeling Blood Flow Circulation in Intracranial Arterial Networks: A Comparative 3D/1D Simulation Study," Annals of Biomedical Engineering, vol. 39, No. 1, pp. 297-309, 2011.

L. Itu et al., "A Patient-Specific Reduced-Order Model for Coronary Circulation," IEEE International Symposium on Biomedical Imaging, Barcelona, Spain, May 2012.

P. A.L. Tonino et al., "Fractional Flow Reserve versus Angiography for Guiding Percutaneous Coronary Intervention," The New England Journal of Medicine, vol. 360, No. 3, pp. 213-224, 2009.

\* cited by examiner

COMPUTATION OF HEMODYNAMIC QUANTITIES FROM ANGIOGRAPHIC DATA

RELATED APPLICATIONS

This application claims the benefit of U.S. Provisional Application No. 61/669,325, filed Jul. 9, 2012, and U.S. Provisional Application No. 61/812,346, filed Apr. 16, 2013. The entire contents of both provisional applications are incorporated herein by reference, except that in the event of any inconsistent disclosure or definition from the present specification, the disclosure or definition herein shall be deemed to prevail.

TECHNICAL FIELD

The present teachings relate generally to the computation of hemodynamic quantities, including but not limited to fractional flow reserve (FFR), which may be used in the assessment of coronary artery disease.

BACKGROUND

Cardiac disease is the leading cause of death for men and women in the United States and accounts for at least 30% of deaths worldwide. Although recent medical advances have resulted in improvements in the diagnosis and treatment of complex cardiac diseases, the incidence of premature morbidity and mortality remains large, at least in part due to a dearth of accurate in vivo and in vitro estimates of patient-specific parameters indicative of a patient's anatomy, physiology, and hemodynamics.

Medical imaging based techniques (e.g., computed tomography, angiography, and the like) may be used in clinical practice for characterizing the severity of stenosis in the coronary arteries. However, the anatomical assessment provided by such techniques is oftentimes inadequate in clinical decision-making. For example, anatomical assessment of the severity of coronary artery stenosis may lead to overestimation or underestimation, neither of which is desirable. On the one hand, overestimation of stenosis severity may lead to unnecessary intervention and subsequent risk of restenosis. On the other hand, underestimation may lead to non-treatment. An accurate functional assessment of a patient's risk of cardiovascular disease may require measurements of pressure and/or flow, which are determined invasively.

One type of invasive measurement used in the determination of FFR values involves the insertion of a pressure wire into a patient's artery. One drawback of using a pressure wire is the possibility of disrupting plaque and triggering a cardiac event in the patient. Another potential problem in using a pressure wire is the risk of perforating the lumen of a blood vessel with the wire. Moreover, the use of a pressure wire is time consuming and may limit a medical practitioner's ability to collect data in real time and apply the data in a clinical setting (e.g., while a patient is in the midst of a procedure). In addition, the use of a pressure wire is simply not feasible with certain patients due to their constitutions and/or severities of disease state.

SUMMARY

The scope of the present invention is defined solely by the appended claims, and is not affected to any degree by the statements within this summary.

Angiography-based methods and systems for computing hemodynamic quantities in accordance with the present teachings involve calculating flow rates and/or changes in pressure in a patient's blood vessel. The hemodynamic quantity—for example, FFR—may be computed based on the calculated flow rates and/or changes in pressure.

By way of introduction, a computer-implemented method for computing a hemodynamic quantity in accordance with the present teachings includes: (a) acquiring angiography data from a patient; (b) calculating, by a processor, a flow and/or a change in pressure in a blood vessel of the patient based on the angiography data; and (c) computing, by the processor, the hemodynamic quantity based on the flow and/or the change in pressure.

A computer-implemented method for computing a fractional flow reserve in accordance with the present teachings includes: (a) acquiring angiography data from a patient, wherein the acquiring includes monitoring movement of a contrast agent through a blood vessel of the patient; (b) calculating, by a processor, a flow based on the angiography data; (c) calculating, by the processor, a change in pressure in the blood vessel of the patient, wherein the blood vessel comprises a stenosis; and (d) computing, by the processor, the fractional flow reserve based on the flow and the change in pressure.

A system for computing a hemodynamic quantity in accordance with the present teachings includes: (a) a processor; (b) a non-transitory memory coupled to the processor; (c) first logic stored in the memory and executable by the processor to cause the processor to acquire angiography data from a patient; (d) second logic stored in the memory and executable by the processor to cause the processor to calculate a flow based on the angiography data; (e) third logic stored in the memory and executable by the processor to cause the processor to calculate a change in pressure in a blood vessel of the patient based on the angiography data; and (f) fourth logic stored in the memory and executable by the processor to cause the processor to compute the hemodynamic quantity based on the flow and/or the change in pressure.

A non-transitory computer readable storage medium in accordance with the present teachings has stored therein data representing instructions executable by a programmed processor for computing a hemodynamic quantity. The storage medium includes instructions for: (a) acquiring angiography data from a patient; (b) calculating a flow based on the angiography data; (c) calculating a change in pressure in a blood vessel of the patient based on the angiography data; and (d) computing the hemodynamic quantity based on the flow and/or the change in pressure.

DETAILED DESCRIPTION

Figure 1:
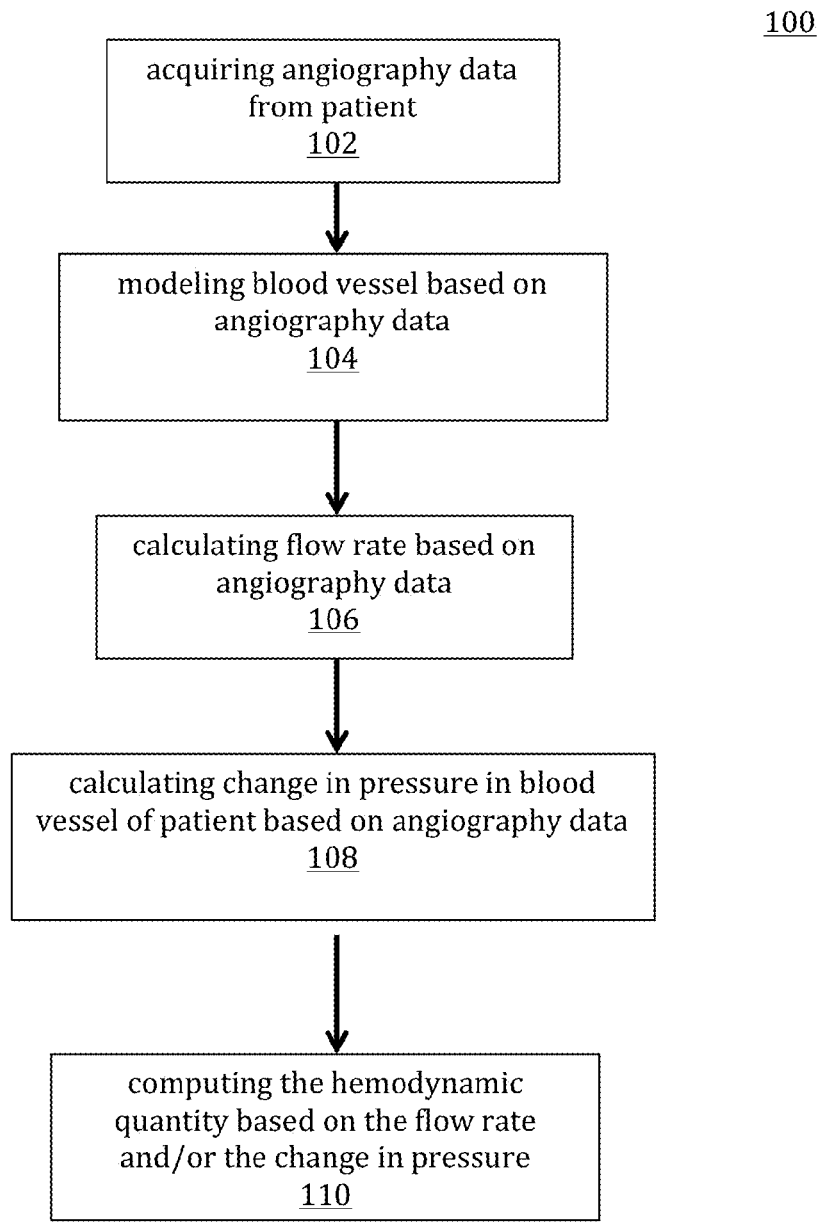
FIG. 1 shows an exemplary flow chart of a representative method for computing hemodynamic quantities.

Angiography-based methods and systems for computing hemodynamic quantities by calculating flow rates and/or changes in pressure in a patient's blood vessel have been discovered and are described herein. The hemodynamic quantities—for example, fractional flow reserve (FFR)—may be computed based on the calculated flow (e.g., flow rates and/or flow velocities) and/or changes in pressure. Angiography-based FFR in accordance with the present teachings is applicable in different scenarios, such as hyperemic states and rest states of a patient. In addition, angiography-based FFR may bypass the use of pressure wires and involve lower radiation exposure and reduced contrast use as compared to conventional methodologies, thereby providing enhanced workflows and reduced costs.

FFR is defined as the ratio of maximum blood flow behind (distal to) a stenosis to normal maximum blood flow in the same blood vessel. The determination of FFR values may be used in coronary catheterization as a functional measure of the hemodynamic significance of a coronary stenosis. At one extreme, an FFR value of 1.00 represents no stenosis within a blood vessel; at the other extreme, an FFR value of 0.00 represents a total blockage. Between these integer limits, FFR values greater than about 0.75 or 0.80 are deemed indicative of non-significant stenosis, while values below the cut-off are deemed hemodynamically significant (i.e. ischemic).

As defined, FFR represents the ratio of flow in a stenosed vessel ($Q^{Stenosis}$) to flow in a normal vessel $Q^{Normal}$) with both of these flows, $Q^{Stenosis}$ and $Q^{Normal}$, being determined at a state of maximal hyperemia. However, the normal vessel referenced in the ratio is hypothetical (e.g., assumes no stenosis). Since such a normal vessel is not, in fact, present, an alternate pressure-based formulation may be used for quantifying FFR. Due to the coronary auto-regulation mechanism, which lowers microvascular resistance, the resting flow remains constant in a range of perfusion pressures.

In order to calculate FFR via pressure measurements, operations are conducted in the maximal hyperemia regime, where the pressure is directly proportional to the flow (e.g., since the myocardial resistance is fixed at its lowest value and can change no further). At maximal hyperemia, as shown in EQN. (1), flow-rate terms can be substituted by appropriate perfusion pressure terms, all of which can be measured in the stenosed vessel (e.g., without reference to a hypothetical "normal" vessel). Resistances cancel out in the numerator and denominator.

$$FFR = \frac{Q_{max}^{Stenosis}}{Q_{max}^{Normal}} \quad (1)$$
$$= \frac{\Delta P^{Stenosis}}{\Delta P^{Normal}}$$
$$= \frac{P_d - P_v}{P_a - P_v}$$
$$= \frac{P_d}{P_{Ao}}$$

In EQN. (1), $P_d$ and $P_a$ are, respectively, average (over the cardiac cycle) distal pressure and aortic pressure during hyperemia. $P_v$ is the venous pressure ($P_v \approx 0$).

Angiography-based FFR in accordance with the present teachings has the potential for addressing a patient population already being examined in a catheterization laboratory (cath lab) due to the severity of their disease. It is to be understood that elements and features of the various representative embodiments described below may be combined in different ways to produce new embodiments that likewise fall within the scope of the present teachings.

By way of general introduction, as shown in FIG. 1, an exemplary method 100 for computing a hemodynamic quantity in accordance with the present teachings includes: (a) acquiring 102 angiography data from a patient; (b) calculating a flow 106 and/or calculating a change in pressure 108 in a blood vessel of the patient based on the angiography data; and (c) computing 110 the hemodynamic quantity based on the flow and/or the change in pressure. In some embodiments, the flow is selected from the group consisting of flow rate, flow velocity, and a combination thereof. In some embodiments, both the flow (e.g., flow rate) and the change in pressure are calculated and, in some embodiments, the hemodynamic quantity is computed based on both the flow and the change in pressure. In some embodiments, the blood vessel has a stenosis.

As used herein, the phrase "hemodynamic quantity" refers broadly to any parameter relating to the flow of blood in the blood vessels. Representative "hemodynamic quantities" in accordance with the present teachings include but are not limited to blood flow velocity, blood pressure (or ratios thereof), heart rate, flow rate, FFR, and the like, and combinations thereof. In some embodiments, the hemodynamic quantity includes FFR. For purposes of illustration, various aspects of the present teachings are described in relation to FFR as a representative hemodynamic quantity. However, it is to be understood that FFR is merely one type of hemodynamic quantity and that the present teachings are not limited thereto.

In some embodiments, a method for computing a hemodynamic quantity in accordance with the present teachings further includes (d) modeling 104 at least a portion of the blood vessel based on the angiography data. In some embodiments, coronary angiography provides anatomical information (e.g., from three-dimensional, symbolic reconstruction of multiple single plane, bi-plane angiography images and/or DynaCT images) that includes the stenosed vessel and, optionally, other parts of the vessel. Moreover, in some embodiments, coronary angiography provides functional information contained in the propagation of contrast agent in the vessels. In some embodiments, an epicardial vessel tree may be reconstructed from multiple single plane, bi-plane angiography and/or DynaCT images. In some embodiments, the three-dimensional reconstruction of stenosis from multiple single plane, bi-plane angiography correlates well with two-dimensional QCA and IVUS measurements, and similar methods may be clinically feasible for the reconstruction of the epicardial vessel tree.

It is to be understood that the relative ordering of some acts shown in the flow chart of FIG. 1 (of, for that matter, in the flow charts shown in FIGS. 3, 4, 9, and/or 10) is meant to be merely representative rather than limiting, and that alternative sequences may be followed. Moreover, it is likewise to be understood that additional, different, or fewer acts may be provided. By way of non-limiting and representative example, in FIG. 1, the act of modeling 104 a blood vessel based on angiography data is shown as preceding the acts of calculating a flow rate 106 and/or calculating a change in pressure 108. However, in alternative embodiments, these acts may occur in a different sequential order and/or one or more of these acts may occur substantially contemporaneously.

In some embodiments, a hemodynamic quantity to be computed is FFR. As further described below, there are multiple scenarios possible for computing FFR from angiography data in accordance with the present teachings, each of which may involve a different approach vis-à-vis modeling and/or computation (e.g., underlying parameter estimation). In some embodiments, representative factors for consideration may include state of the patient (e.g., resting state or drug-induced hyperemia) during angiographic acquisition; accuracy of flow estimation from contrast propagation; accuracy of three-dimensional symbolic reconstruction of a stenosis, stenosed vessel, and/or branching vessels; availability of prior patient data for cardiac function estimation; and the like, and combinations thereof. In some embodiments, FFR estimation is achieved based on rest-state angiography data. In other embodiments, FFR estimation is achieved based on angiography data acquired during drug-induced hyperemia.

In some embodiments, at least a portion of the angiography data is acquired when the patient is at rest whereas, in other embodiments, at least a portion of the angiography data is acquired when the patient is in a state of hyperemia. In further embodiments, at least a first portion of the angiography data is acquired when the patient is at rest, and at least a second portion of the angiography data is acquired when the patient is in a state of hyperemia.

X-ray angiography may be performed to estimate the anatomic severity of a coronary lesion of interest. At least one view—and, in some embodiments, more than one view—may be acquired via angiography. As further described below, two or more views of the same blood vessel may be acquired to enable subsequent three-dimensional reconstruction of the blood vessel and stenosis geometry.

Figure 3:
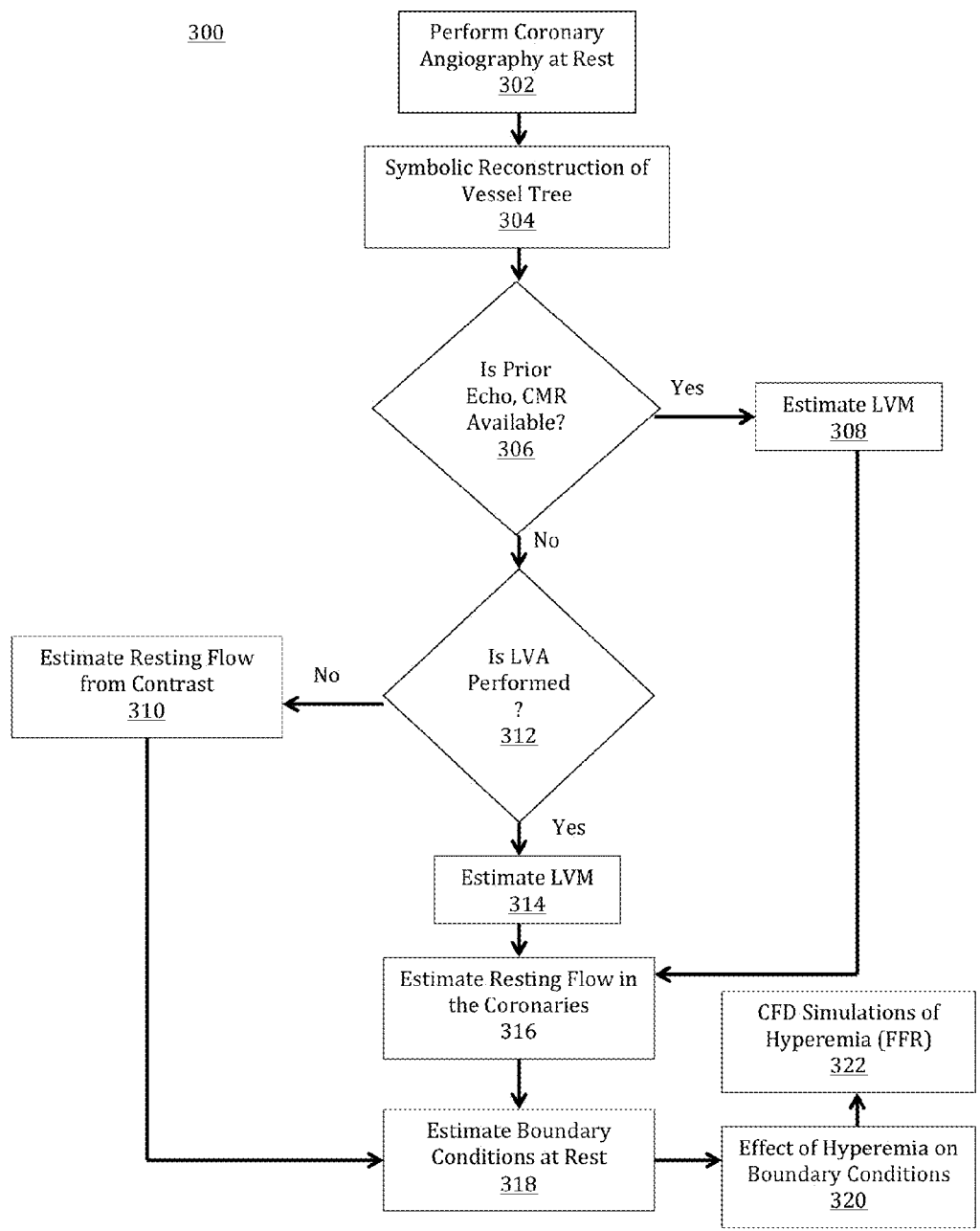
FIG. 3 shows an exemplary flow chart of a representative method of computing FFR from angiography data acquired during a resting state of a patient.

FIG. 3 shows an exemplary flow chart of a representative method 300 of computing FFR from angiography data acquired during a resting state of a patient. At block 302, coronary angiography may be performed on a patient at rest. At block 304, a symbolic reconstruction of the vessel tree may be performed from the acquired data. If only one image is acquired at block 302, the reconstruction may be a two-dimensional representation. If more than one image is acquired at block 302, a two or three-dimensional reconstruction may be performed. Three-dimensional reconstruction of the stenosed vessel may be performed from multiple views from monoplane, bi-plane, and/or rotational angiography. Calibration and temporal phase matching may be performed to minimize discrepancies in the reconstruction.

At block 306, if prior echocardiography, cardiac magnetic resonance (CMR), and/or cardiac computed tomography (CT) data are available, the workflow may proceed to block 303 and an approximate mass of the heart tissue (e.g., left ventricular mass or LVM) may be estimated. If prior echo and/or CMR data are not available, the workflow may proceed to block 312 to determine if left ventricular angiography (LVA) has been performed. If LVA has not been performed, the workflow may proceed to block 310 at which the rest-state flow rate may be estimated from the movement of contrast agent through the patient's blood vessels as described in U.S. patent application publication no. 2012/0072190 A1 (assigned to the assignee of the present application), and to block 318 at which rest-state boundary conditions may be estimated. If, on the other hand, LVA has been performed, the workflow may proceed to block 314 and an estimate of LVM may be made. At block 316, a rest-state flow rate in the coronaries may be estimated and, at block 318, rest-state boundary conditions may be estimated as described above. At block 320, the effect of hyperemia on the boundary conditions may be determined (e.g., by multiplying the rest-state flow rate by a factor rCBF, as further described below in reference to EQN. (17)) and, at block 322, computational flow dynamics (CFD) simulations at hyperemia may be performed to determine the FFR.

In computations of FFR from CTA data, the LVM may be used for estimating the total resting coronary flow, which may be used for the initial estimate of the boundary conditions for the myocardial microvascular bed during rest, which may then be modified to achieve the hyperemia conditions. For computations of FFR from angiography data, multiple options are available for the assessment. For example, in a first option, LV angiography in addition to coronary angiography may be performed, and LVM as well as other quantities of interest (e.g., stroke volume, LVEF) may be determined. In a second option, the parameter estimation procedure for boundary condition estimation may be modified so that it uses the additional hemodynamic information present in the angiographic sequence (e.g., the propagation of contrast agent in the vessel tree) to estimate rest-state boundary conditions. As shown in EQN. (21) below, pressure or flow rate may be specified to properly constrain the equations. In a third option, the angiography may be performed during hyperemia, and the hyperemic flow may be estimated from contrast propagation and used to compute the hyperemic pressure drop and, in turn, the FFR value.

Figure 8:
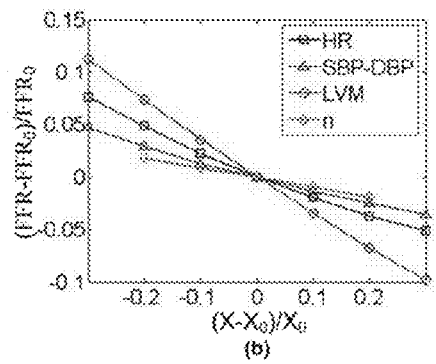
FIG. 8 shows a plot of sensitivity of FFR computations with respect to patient-specific parameters.

In some embodiments, if the LVM is available from prior scans (e.g., echocardiography, cardiac MR, cardiac CT, etc.), then LVM can be used for estimating rest-state coronary flow rates. As shown by the plot of FFR computation sensitivity with respect to patient data in FIG. 8, analysis suggests that an estimation of LVM within a +/−10% error results in approximately +/−3.5 to 4% variation in the computed FFR value. In FIG. 8, HR, SBP-DBP, LVM, and n represent, respectively, heart rate, systolic blood pressure-diastolic blood pressure, left ventricular mass, and a patient-specific parameter determined via clinical studies.

In other embodiments, if the image acquisition protocol does not allow LVA acquisition, the above-described second option may be used. X-ray based videodensiometric techniques may be used to estimate coronary flow. Depending on whether the flow rate is estimated (a) at rest or at hyperemia, (b) in the main vessel or in the stenosed vessel, and (c) as a time-varying value or a mean value, the parameter estimation and the subsequent flow computation procedure may be adapted to optimally incorporate the information and compute FFR.

Based on the flow estimation technique and the availability of high-frame-rate angiography data, the following five scenarios are possible: (1) fairly accurate time-varying flow estimated in the stenosed vessel; (2) fairly accurate time-varying flow estimated in the main vessel; (3) fairly accurate mean flow estimated in the stenosed vessel; (4) fairly accurate mean flow estimated in the main vessel; and (5) noisy time-varying/mean flow estimated in the stenosed or main vessel. Scenarios 1 through 4 may be addressed through a parameter estimation process for determining rest boundary conditions. Scenario 5 may be addressed through a slightly different approach, as described further below in reference to FIG. 5.

Figure 4:
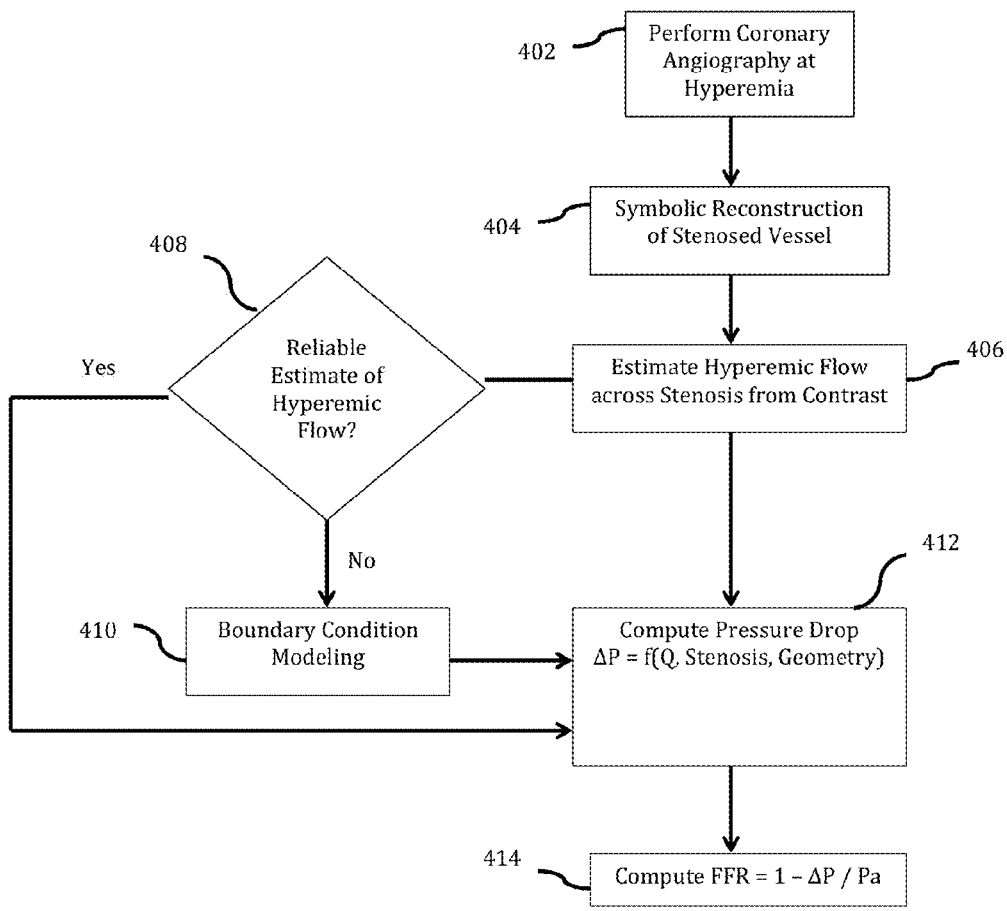
FIG. 4 shows an exemplary flow chart of a representative method of computing FFR from angiography data acquired during a hyperemic state of a patient.

FIG. 4 shows an exemplary flow chart of a representative method 400 of computing FFR from angiography data acquired during a hyperemic state of a patient. At block 402, coronary angiography may be performed on a patient in a hyperemic state. At block 404, a symbolic reconstruction of the stenosed vessel may be performed from the acquired data. At block 406, a rough estimate of hyperemic flow rate across the stenosis may be performed based on contrast data. If the estimate of hyperemic flow rate is judged at block 408 to be reliable, the workflow may proceed to block 412 and the pressure drop may be computed. The estimate may be deemed reliable if the frame-rate of the angiographic estimation allows the contrast to be tracked over time, and the image quality is suitable for clinical interpretation. The change in pressure computed in block 412 is a function of flow rate and stenosis geometry. If, on the other hand, the hyperemic flow cannot be estimated reliably in the stenosed vessel, then boundary condition modeling (as in FIG. 3) can be performed at block 410, followed by a flow computation at block 414 to determine the pressure-drop.

If a three-dimensional model of a stenosis is available—which typically is not the case with angiographic data—then changes in pressure (e.g., pressure drops) may be computed by three-dimensional CFD computations. When accurate three-dimensional data are not available, the shape of the stenosis may be characterized by quantitative coronary angiography (QCA)-like measurements, as well as other geometric measurements including but not limited to proximal vessel diameter, proximal vessel area, distal vessel diameter, distal vessel area, minimal lumen diameter, minimal lumen area, length of the stenosis, entrance angle, exit angle, percent diameter stenosis, percent area stenosis, and the like, and combinations thereof. Using such a model with the hyperemic flow-rate, the pressure drop and, therefore, FFR may be computed as described below. It is to be understood, however, that the exemplary pressure drop model and associated formulae described below are merely representative, and that alternative pressure drop models and equations for computing hemodynamic quantities such as FFR may be employed without departing from the overall approach described.

Figures 5, 6:
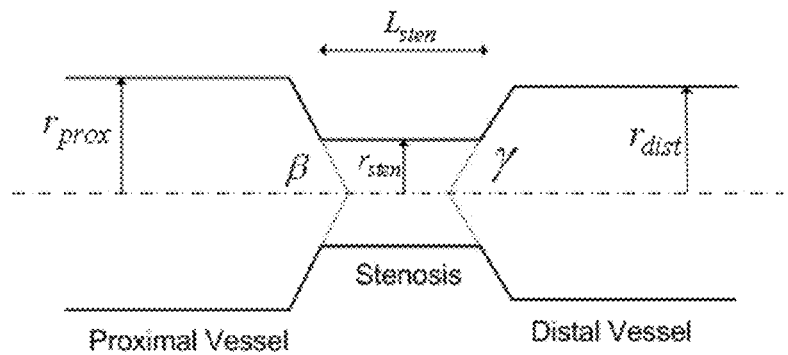
FIG. 5 shows plots of sensitivity and specificity of FFR estimations for different flow rate (Q) perturbations.
FIG. 6 shows an exemplary two-dimensional schematic representation of a stenotic vessel.

FIG. 6 shows an exemplary two-dimensional schematic representation of a stenotic vessel. From a fluid dynamics aspect, as shown in EQN. (2), the pressure drop across the configuration shown in FIG. 6 is composed of two different parts: "major loss" and "minor loss," each of which corresponds to a different mechanism:

$$\Delta p_{stenosis} = \Delta p_{major} + \Delta p_{minor} \quad (2).$$

The major loss is the pressure loss due to the skin frictions, and may be computed as shown below for a pipe configuration.

EQN. (3) may be used for the fully developed pipe flow:

$$\Delta p_{major} = \int_0^L \frac{8\pi\mu}{CSA^2} Q\,dx. \quad (3)$$

EQN. (4) may be used for the transit flow with entrance effects:

$$\Delta p_{major} = \frac{\rho Q^2}{2CSA} \frac{96}{5} \int_\alpha^1 \frac{(1+4\theta+9\theta^2+4\theta^3)}{\theta(3+2\theta)(3+2\theta+\theta^2)} d\theta. \quad (4)$$

In EQN. (4), CSA is the cross section of the vessel, which is a function of x, Q is the volume flow rate, μ is the dynamic viscosity, and α is the inviscid core which is computed as shown in EQN. (5):

$$\frac{\pi\mu L}{4\rho Q} = \frac{1}{4} \int_\alpha^1 \frac{(1-\theta)(6+\theta)(1+4\theta+9\theta^2+4\theta^3)}{5\theta(3+2\theta)(3+2\theta+\theta^2)} d\theta. \quad (5)$$

The "minor loss" is the pressure loss due to the flow separation, bending and mixing. For the current configuration, the minor loss can be further decomposed into three terms: $\Delta p_{convection}$ (pressure drop due to convection), $\Delta p_{contraction}$ (pressure drop due to sudden contraction), and $\Delta p_{expansion}$ (pressure drop due to sudden expansion), as shown in EQN. (6):

$$\Delta p_{minor} = \Delta p_{convection} + \Delta p_{contraction} + \Delta p_{expansion} \quad (6).$$

$\Delta p_{convection}$ is due purely to Bernoulli effects resulting from the different cross section areas between inlet and outlet, and is computed as shown in EQN. (7):

$$\Delta P_{convective} = \frac{\rho Q^2}{2}\left(\frac{1}{CSA_{outlet}^2} - \frac{1}{CSA_{inlet}^2}\right). \quad (7)$$

$\Delta p_{contraction}$ is due to "vena contracta" effects resulting from the sudden contraction inside the pipe, and may be computed based on Reynolds number Re and inlet angles β.

For Laminar flow (Re≤300~500) EQN. (8) may be used for fully developed flow:

$$\Delta p_{contraction} = \frac{\rho Q^2}{2} \frac{6}{\pi}\left(\frac{(1/R_{stenosis}^4) - (1/R_{stenosis}^2 R_{proxi}^2)}{Re_{stenosis}}\right), \quad (8)$$

and EQN. (9) may be used for flow with entrance effects:

$$\Delta p_{contraction} = \left(\frac{1}{2}\rho Q^2\right)\frac{1}{2}\left(\frac{1}{CSA_{sten}^{8/3}} - \frac{1}{CSA_{proxi}CSA_{sten}^{5/3}}\right)^{3/4}. \quad (9)$$

For turbulent flow (Re>300~500), EQN. (10) may be used for β<45°.

$$\Delta p_{contraction} = 0.8\ \sin\left(\frac{\alpha}{2}\right)\left(\frac{1}{2}\rho Q^2\right)\left(\frac{1}{CSA_{proxi}} - \frac{1}{CSA_{stenosis}}\right), \quad (10)$$

and EQN. (11) may be used for β>45°:

$$\Delta p_{contraction} = 0.5\sqrt{\sin\left(\frac{\beta}{2}\right)}\left(\frac{1}{2}\rho Q^2\right)\left(\frac{1}{CSA_{proxi}} - \frac{1}{CSA_{stenosis}}\right). \quad (11)$$

$\Delta p_{expansion}$ is due to the flow separation and mixing resulting from sudden expansion, and may be computed based on Reynolds number Re and inlet angles γ.

For Laminar flow (Re≤300~500) EQN. (12) may be used for fully developed flow:

$$\Delta p_{expansion} = \frac{1}{2}\rho Q^2\left(\frac{1}{CSA_{sten}} - \frac{1}{CSA_{distal}}\right)\left(\frac{1}{CSA_{sten}} - \frac{1}{3}\frac{1}{CSA_{distal}}\right), \quad (12)$$

and EQN. (13) may be used for flow with entrance effects:

$$\Delta p_{expansion} = \frac{1}{2}\rho Q^2 \left(\frac{1}{CSA_{sten}} - \frac{1}{CSA_{distal}}\right)^2. \quad (13)$$

For turbulent flow (Re>300~500), EQN. (14) may be used for $\gamma<45°$.

$$\Delta p = 2.6 \sin\left(\frac{\gamma}{2}\right)\left(\frac{1}{2}\rho Q^2\right)\left(\frac{1}{CSA_{sten}} - \frac{1}{CSA_{distal}}\right)^2, \quad (14)$$

and EQN. (15) may be used for $\gamma>45°$:

$$\Delta p_{expansion} = \frac{1}{2}\rho Q^2 \left(\frac{1}{CSA_{sten}} - \frac{1}{CSA_{distal}}\right)^2. \quad (15)$$

In some embodiments, the flow rate calculated in accordance with the present teachings includes a rest-state flow rate. In some embodiments, the rest-state flow rate is estimated from the LVM (e.g., when the LVM is available from prior echo, CMR, and/or the like) and, in some embodiments, the rest-state flow rate is estimated from contrast data. In some embodiments, the flow rate calculated in accordance with the present teachings includes a hyperemic flow rate. In some embodiments, the flow rate calculated in accordance with the present teachings includes each of a rest-state flow rate and a hyperemic flow rate. In some embodiments, the flow rate calculated in accordance with the present teachings includes a hyperemic flow, which is derived from a rest-state flow rate (e.g., a previously calculated rest-state flow rate). In some embodiments, the angiography data is acquired at a first physiological state of the patient (e.g., a rest state), and the flow rate corresponds to a second physiological state of the patient (e.g., a hyperemic state) that is different from the first physiological state of the patient. In some embodiments, the rest flow rate is estimated from contrast.

In some embodiments, the calculating of the flow rate is based on movement of a contrast agent in the blood vessel. In other embodiments, the calculating of the flow rate is based on an estimate of the left ventricular mass (LVM).

In some embodiments, calculations of flow rate are performed using a full-order model for computations. In other embodiments, calculations of flow rate are performed using a reduced-order model for computations. In some embodiments, reduced-order flow computations may be desirable for reducing computation time (e.g., in clinical settings where rapid acquisition of information regarding a patient may be applied in real time during a procedure). In the case of a reduced-order model, coronary vessels may be represented as axi-symmetric segments by a centerline and cross-sectional area at each point on the centerline tree. CFD computations on a reduced-order model are accurate for estimation of pulsatile flow and pressure as compared to three-dimensional models. Although reduced-order modeling may be unsuitable for computing wall-shear stress and some complex flow features (e.g., flow separation), the reduced-order model is reliably applicable to computations of FFR because FFR, by definition, involves mean pressure over the cardiac cycle (e.g., distal and proximal to the stenosis), which presupposes appropriate estimations of the upstream and downstream boundary conditions. Of course, if accurate three-dimensional geometry may be extracted from angiographic images, then the data can be used for full-order, three-dimensional flow computations.

FIG. 5 shows plots of sensitivity and specificity of FFR estimations for different flow rate (Q) perturbations to demonstrate the effect of noisy flow rate estimations on FFR computations. For a given stenosis, the higher the average flow through the lesion, the higher will be the pressure drop, thereby resulting in a smaller FFR value. Consistent overestimation (underestimation) of the flow rate results in underestimation (overestimation) of the FFR value. To analyze the effect of flow rate variation on the final outcome (e.g., whether FFR>0.75 or FFR<0.75), hyperemic pressure drop was computed in 100 artificially generated stenoses with different lengths, tapering, and percent diameter reduction. For the baseline flow rate, 37 were deemed hemodynamically significant (FFR<0.75), while 63 were deemed non-significant (FFR>0.75). Next, the flow rates were changed by ±2%, ±4%, ±6%, ±8%, and ±10%, and the FFR was recomputed. The sensitivity and specificity of the current CFD-based FFR algorithm with respect to the flow rate perturbation is shown in FIG. 5. The results suggest that (a) CFD-based FFR based on the current algorithm is mildly sensitive with respect to flow rate variation; and (b) the sensitivity is well within the grey-zone variation (0.75<FFR<0.80) of cut-off value for a ±10% variation in flow rate. Therefore, the predictive value of the computed FFR is minimally affected by this variation. It is noted that to improve the initial estimate of Q, the contrast propagation (advection-diffusion) can be iteratively computed, and the observed and measured time-intensity curves compared until a good agreement is obtained.

In connection with computation of hemodynamic quantities such as FFR, a representative determination of boundary conditions as described above in references to FIGS. 3 and 4 is now provided.

Figure 9:
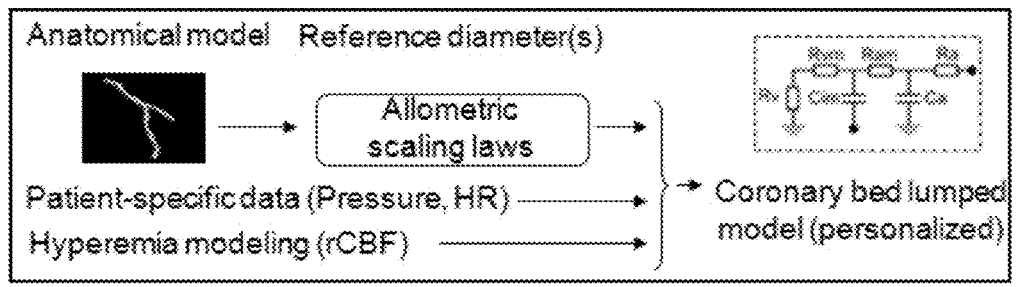
FIG. 9 shows a schematic representation of an exemplary procedure for determining outlet boundary conditions.

FIG. 9 shows a schematic representation of an exemplary procedure for determining outlet boundary conditions. A good starting point for estimating the normal rest flow rate of a diseased vessel, $(Q_r)_i$, is the generalization of Murray's law, as shown in EQN. (16):

$$(Q_r)_i = k \cdot k_i^n \quad (16).$$

In EQN. (16), $r_i$ is the radius of the healthy part of the vessel.

Using a population average hyperemic-to-rest flow rate ratio, the normal hyperemic flow rate of the diseased vessel may be computed, as shown in EQN. (17):

$$(Q_h)_i = rCBF \cdot (Q_r)_i, \quad (17).$$

In EQN. (17), rCBF represents the ratio of coronary blood flow at hyperemia to coronary blood flow at rest.

The rest mean arterial pressure ($MAP_r$) may be computed from systolic blood pressure (SBP), diastolic blood pressure (DBP), and heart rate (HR), as shown in EQN. (18):

$$MAP_r = DBP + \left[\frac{1}{3} + (HR \cdot 0.0012)\right] \cdot (SBP - DBP). \quad (18)$$

The hyperemic mean arterial pressure, $MAP_h$, may be estimated according to EQN. (19):

$$MAP_h = MAP_r - \Delta MAP \quad (19),$$

where $\Delta MAP$ is a population average rest-to-hyperemic pressure difference, after the administration of intracoronary adenosine (5-10 mmHg). Assuming an average venous pressure, $P_v$, of 5 mmHg, the total hyperemic microvascular resistance may be determined according to EQN. (20):

$$(R_{t-h})_i = \frac{MAP_h - P_v}{(Q_h)_i}, \quad (20).$$

Figure 10:
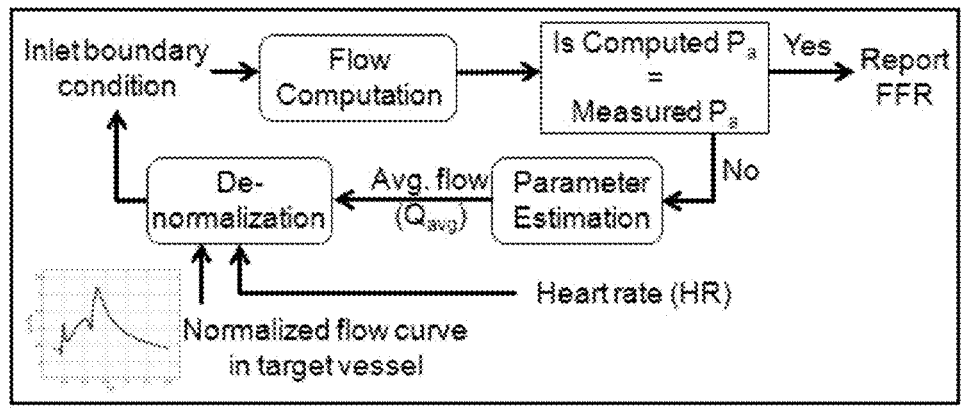
FIG. 10 shows a schematic representation of an exemplary workflow for model personalization and flow computation.

Model personalization via parameter estimation is now described in reference to FIG. 10, which shows a schematic representation of an exemplary workflow for model personalization and flow computation.

Since the blood vessel contains a stenosis and the stenosis introduces an additional resistance, the actual flow rate is smaller than the normal flow rate $(Q_h)_i$. To obtain the flow rate in the diseased state, a tuning procedure is applied in which the nonlinear equation shown in EQN. (21) is solved:

$$f((Q_h)_i) = (MAP_h)_{comp} = (MAP_h)_{ref} = 0 \quad (21).$$

In EQN. (21), $(Q_h)_i$ represents the tuned parameter, $(MAP_h)_{comp}$ represents the computed mean arterial pressure of the coronary vessel, and $(MAP_h)_{ref}$ represents the reference value, computed with EQN. (18). As a result, the average flow rate applied at the inlet is tuned until the desired average pressure is obtained.

Assuming a certain value for n (between 2.33 and 3.0), the only unknown for the above-described method is the constant k in EQN. (16). The constant k may be determined, for example, by minimizing the error between measured and computed FFR values once a large set of patient data is available.

A method for computing a fractional flow reserve in accordance with the present teachings includes (a) acquiring (102') angiography data from a patient, wherein the acquiring (102') includes monitoring movement of a contrast agent through a blood vessel of the patient; (b) calculating a flow rate (106') based on the angiography data; (c) calculating a change in pressure (108') in the blood vessel of the patient, wherein the blood vessel comprises a stenosis; and (d) computing (110') the fractional flow reserve based on the flow rate and the change in pressure.

In some embodiments, a method for computing a hemodynamic quantity (e.g., fractional flow reserve) in accordance with the present teachings is implemented using a computer and, in some embodiments, one or a plurality of the acts of (i) acquiring angiography data from a patient, (ii) calculating a flow rate and/or a change in pressure in a blood vessel of the patient based on the angiography data, (iii) computing the hemodynamic quantity based on the flow rate and/or the change in pressure, and/or (iv) modeling at least a portion of the blood vessel based on the angiography data described above are performed by one or a plurality of processors.

Figure 2:
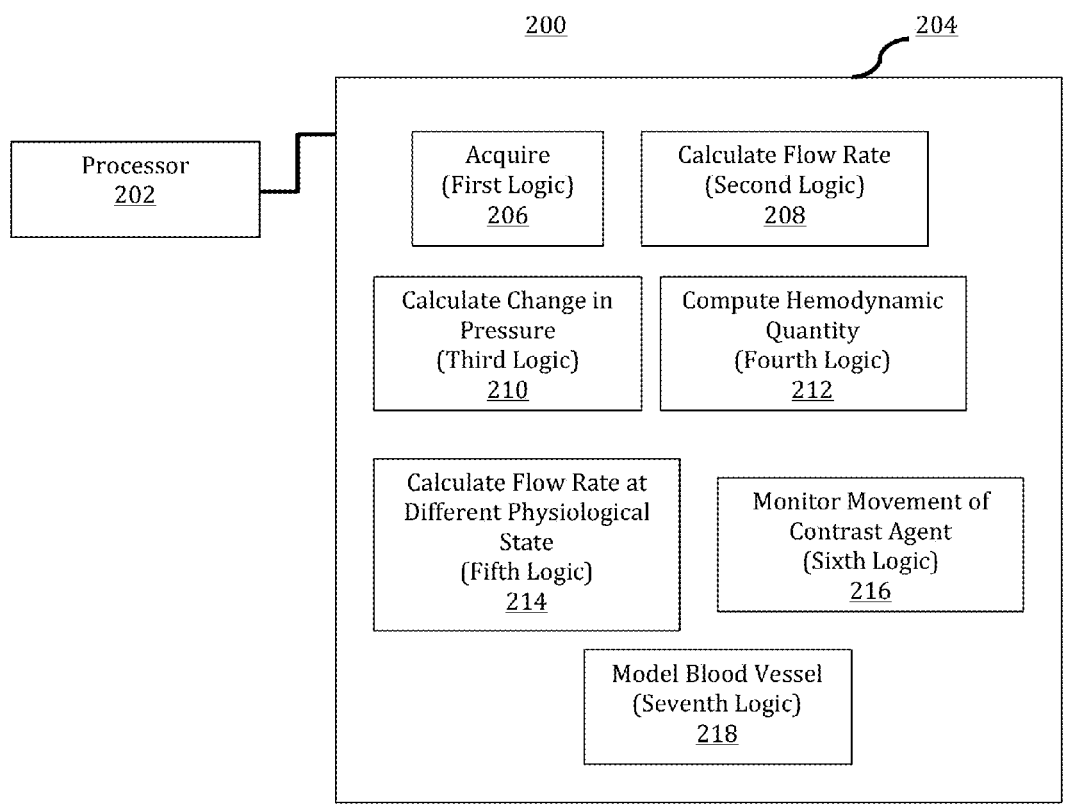
FIG. 2 shows a block diagram of an exemplary implementation of a system for computing hemodynamic quantities.

FIG. 2 shows an exemplary system 200 for computing a hemodynamic quantity in accordance with the present teachings. The system 200 includes a processor 202; a non-transitory memory 204 coupled to the processor 202; first logic 206 stored in the memory 204 and executable by the processor 202 to cause the processor 202 to acquire angiography data from a patient (e.g., access stored data or cause scanning of the patient); second logic 208 stored in the memory 204 and executable by the processor 202 to cause the processor 202 to calculate a flow rate based on the angiography data; third logic 210 stored in the memory 204 and executable by the processor 202 to cause the processor 202 to calculate a change in pressure in a blood vessel of the patient based on the angiography data; and fourth logic 212 stored in the memory 204 and executable by the processor 202 to cause the processor 202 to compute the hemodynamic quantity based on the flow rate and/or the change in pressure.

In some embodiments, as shown in FIG. 2, the system 200 further includes fifth logic 214 stored in the memory 204 and executable by the processor 202 to cause the processor 202 to calculate the flow rate at a second physiological state of the patient that is different from a first physiological state of the patient at which the angiography data is acquired. In some embodiments, as further shown in FIG. 2, the system 200 further includes sixth logic 216 stored in the memory 204 and executable by the processor 202 to cause the processor 202 to monitor movement of a contrast agent in the blood vessel. In some embodiments, the system 200 further includes seventh logic 218 stored in the memory 204 and executable by the processor 202 to cause the processor 202 to model at least a portion of the blood vessel based on the angiography data. In some embodiments, a system 200 in accordance with the present teachings further includes only one, all, or a subset of fifth logic 214, sixth logic 216, and seventh logic 218.

A non-transitory computer readable storage medium in accordance with the present teachings has stored therein data representing instructions executable by a programmed processor for computing a hemodynamic quantity. In some embodiments, the storage medium includes instructions for: acquiring angiography data from a patient; calculating a flow rate based on the angiography data; calculating a change in pressure in a blood vessel of the patient based on the angiography data; and computing the hemodynamic quantity based on the flow rate and/or the change in pressure.

One skilled in the art will appreciate that one or more modules or logic described herein may be implemented using, among other things, a tangible computer-readable medium comprising computer-executable instructions (e.g., executable software code). Alternatively, modules may be implemented as software code, firmware code, hardware, and/or a combination of the aforementioned. For example the modules may be embodied as part of a medical imaging apparatus in a health care institution.

Figure 7:
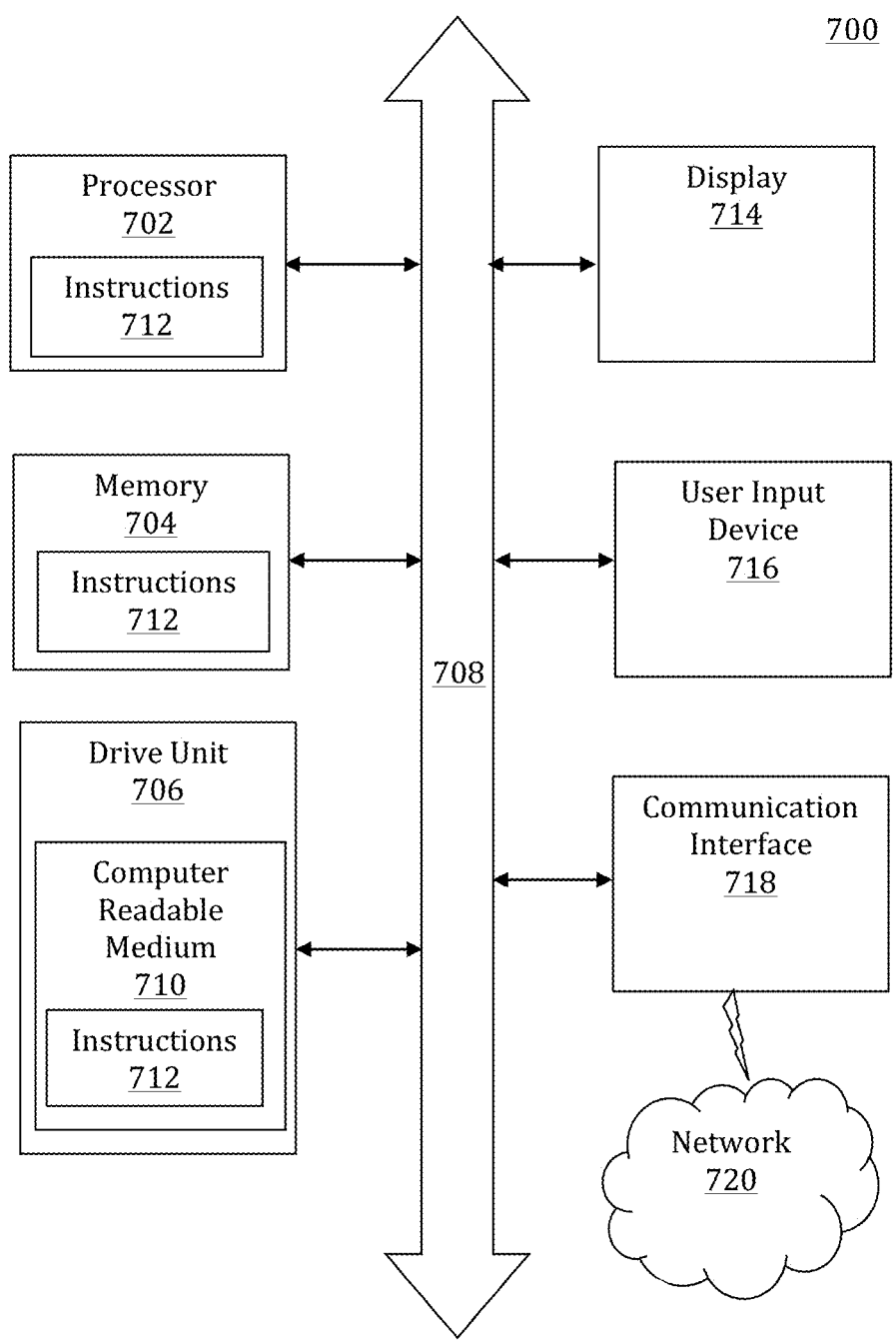
FIG. 7 shows an exemplary general computer system for use in accordance with the present teachings.

Referring to FIG. 7, an illustrative embodiment of a general computer system 700 is shown. The computer system 700 can include a set of instructions that can be executed to cause the computer system 700 to perform any one or more of the methods or computer based functions disclosed herein. The computer system 700 may operate as a standalone device or may be connected (e.g., using a network) to other computer systems or peripheral devices. Any of the components discussed above, such as the processor 202, may be a computer system 700 or a component in the computer system 700.

In a networked deployment, the computer system 700 may operate in the capacity of a server or as a client user computer in a client-server user network environment, or as a peer computer system in a peer-to-peer (or distributed) network environment. The computer system 700 can also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular embodiment, the computer system 700 can be implemented using electronic devices that provide voice, video or data communication. Further, while a single computer system 700 is illustrated, the term "system" shall also be taken to include any collection of systems or sub-systems that individually or jointly execute a set, or multiple sets, of instructions to perform one or more computer functions.

As illustrated in FIG. 7, the computer system 700 may include a processor 702, such as a central processing unit (CPU), a graphics-processing unit (GPU), or both. The processor 702 may be a component in a variety of systems. For example, the processor 702 may be part of a standard personal computer or a workstation. The processor 702 may be one or more general processors, digital signal processors, application specific integrated circuits, field programmable gate arrays, servers, networks, digital circuits, analog circuits, combinations thereof, or other now known or later developed devices for analyzing and processing data. The processor 702 may implement a software program, such as code generated manually (i.e., programmed).

The computer system 700 may include a memory 704 that can communicate via a bus 708. The memory 704 may be a main memory, a static memory, or a dynamic memory. The memory 704 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one embodiment, the memory 704 includes a cache or random access memory for the processor 702. In alternative embodiments, the memory 704 is separate from the processor 702, such as a cache memory of a processor, the system memory, or other memory. The memory 404 may be an external storage device or database for storing data. Examples include a hard drive, compact disc (CD), digital video disc (DVD), memory card, memory stick, floppy disc, universal serial bus (USB) memory device, or any other device operative to store data. The memory 704 is operable to store instructions executable by the processor 702. The functions, acts or tasks illustrated in the figures or described herein may be performed by the programmed processor 702 executing the instructions 712 stored in the memory 704. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown, the computer system 700 may further include a display unit 714, such as a liquid crystal display (LCD), an organic light emitting diode (OLED), a flat panel display, a solid state display, a cathode ray tube (CRT), a projector, a printer or other now known or later developed display device for outputting determined information. The display 714 may act as an interface for the user to see the functioning of the processor 702, or specifically as an interface with the software stored in the memory 704 or in the drive unit 706.

Additionally, the computer system 700 may include an input device 716 configured to allow a user to interact with any of the components of system 700. The input device 716 may be a number pad, a keyboard, or a cursor control device, such as a mouse, or a joystick, touch screen display, remote control or any other device operative to interact with the system 700.

In a particular embodiment, as depicted in FIG. 7, the computer system 700 may also include a disk or optical drive unit 706. The disk drive unit 706 may include a computer-readable medium 710 in which one or more sets of instructions 712, e.g. software, can be embedded. Further, the instructions 712 may embody one or more of the methods or logic as described herein. In a particular embodiment, the instructions 712 may reside completely, or at least partially, within the memory 704 and/or within the processor 702 during execution by the computer system 700. The memory 704 and the processor 702 also may include computer-readable media as discussed above.

The present disclosure contemplates a computer-readable medium that includes instructions 712 or receives and executes instructions 712 responsive to a propagated signal, so that a device connected to a network 720 can communicate voice, video, audio, images or any other data over the network 720. Further, the instructions 712 may be transmitted or received over the network 720 via a communication interface 718. The communication interface 718 may be a part of the processor 702 or may be a separate component. The communication interface 718 may be created in software or may be a physical connection in hardware. The communication interface 718 is configured to connect with a network 720, external media, the display 714, or any other components in system 700, or combinations thereof. The connection with the network 720 may be a physical connection, such as a wired Ethernet connection or may be established wirelessly as discussed below. Likewise, the additional connections with other components of the system 700 may be physical connections or may be established wirelessly.

The network 720 may include wired networks, wireless networks, or combinations thereof. The wireless network may be a cellular telephone network, an 802.11, 802.16, 802.20, or WiMax network. Further, the network 720 may be a public network, such as the Internet, a private network, such as an intranet, or combinations thereof, and may utilize a variety of networking protocols now available or later developed including, but not limited to TCP/IP based networking protocols.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein. The computer readable medium can be a machine-readable storage device, a machine-readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

Although the present specification describes components and functions that may be implemented in particular embodiments with reference to particular standards and protocols, the invention is not limited to such standards and protocols. For example, standards for Internet and other packet switched network transmission (e.g., TCP/IP, UDP/IP, HTML, HTTP, HTTPS) represent examples of the state of the art. Such standards are periodically superseded by faster or more efficient equivalents having essentially the same functions. Accordingly, replacement standards and protocols having the same or similar functions as those disclosed herein are considered equivalents thereof.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and anyone or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including, by way of example, semiconductor memory devices (e.g., EPROM, EEPROM, and flash memory devices); magnetic disks (e.g., internal hard disks or removable disks); magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a device having a display, for example, a CRT (cathode ray tube) or LCD (liquid crystal display) monitor, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 CFR §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The following documents contain additional information that may be used in implementing various aspects of the present teachings: (1) Neubauer et al. "Clinical Feasibility of a Fully Automated 3D Reconstruction of Rotational Coronary X-Ray Angiograms," *Circ. Cardiovasc. Interv.*, 2010, 3, 71-79; (2) Tak. "Ejection Fraction Derived by Noninvasive Modalities Versus Left Ventricular Angiographic Determination," *Clinical Medicine & Research*, 2005, 3, No. 2: 61-62; (3) Molloi et al. "Regional Volumetric Coronary Blood Flow Measurement by Digital Angiography: In Vivo Validation," *Acad. Radiol.*, 2004, 11, No. 7, 757-66; (4) Grinberg et al. "Modeling Blood Flow Circulation in Intracranial Arterial Networks: A Comparative 3D/1D Simulation Study," *Annals of Biomedical Engineering*, 2011, 39, No. 1, 297-309; (5) Itu et al. "A Patient-specific Reduced-order Model for Coronary Circulation," *IEEE International Symposium on Biomedical Imaging*, Barcelona, Spain, May 2012; (6) Schuurbiers et al. "In vivo validation of CAAS QCA-3D coronary reconstruction using fusion of angiography and intravascular ultrasound (ANGUS)," *Catheter Cardiovasc. Interv.*, 2009, 73, No. 5, 620-626; (7) U.S. patent application Ser. No. 13/794,113 filed Mar. 11, 2013 entitled "Method and System for Non-invasive Functional Assessment of Coronary Artery Stenosis"; (8) International PCT patent application no. PCT/US2013/030732 filed Mar. 13, 2013 entitled "Framework for Personalization of Coronary Flow Computations during Rest and Hyperemia"; (9) Toino et al., "Fractional flow reserve versus angiography for guiding percutaneous coronary intervention," *New Engl. J. Med.*, 2009, 360, 213-24; (10) Wilson et al., "Effects of adenosine on human coronary arterial circulation," *Circulation*, 1990, 82, No. 5, 1595-606. The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A computer-implemented method for computing a hemodynamic quantity, the method comprising:

acquiring angiography data from a patient at a first physiological state of the patient, the first physiological state being the patient at rest;

calculating, by a processor, a first flow in a blood vessel of the patient based on the angiography data, wherein the first flow corresponds to the patient at rest, the first flow comprising rest-state flow;

estimating boundary conditions for the patient at rest;

calculating, by the processor, a second flow as hyperemic flow in a blood vessel based on scaling the first flow by a flow rate scalar from the first physiological state to a second physiological state, the second physiological state being a hyperemic state of the patient and the flow rate scalar being a hyperemic-to-rest flow rate ratio;

computing, by the processor, a fractional flow reserve as the hemodynamic quantity based on the calculated hyperemic flow; and reporting the fractional flow reserve to assess coronary artery disease in the patient.

2. The computer-implemented method of claim 1 wherein the blood vessel comprises a stenosis.

3. The computer-implemented method of claim 1 further comprising calculating both the hyperemic flow and a change in pressure.

4. The computer-implemented method of claim 1 wherein the calculating of the hyperemic flow is based on movement of a contrast agent in the blood vessel.

5. The computer-implemented method of claim 1 further comprising modeling at least a portion of the blood vessel based on the angiography data.

6. The computer-implemented method of claim 1 wherein the hyperemic flow is derived from the rest-state flow.

7. The computer-implemented method of claim 1 wherein computing the fractional flow reserve comprises computing with computational fluid dynamics using the hyperemic flow calculated from the rest-state flow.

8. A computer-implemented method for computing a fractional flow reserve, the method comprising:

acquiring angiography data from a patient at a resting state of the patient, wherein the acquiring comprises monitoring movement of a contrast agent through a blood vessel of the patient;

calculating, by a processor, a first flow in a blood vessel of the patient based on the angiography data, wherein the first flow corresponds to the patient at rest, the first flow comprising rest-state flow;

calculating, by a processor, a hyperemia flow based on the angiography data, wherein the hyperemia flow corresponds to a hyperemia state of the patient that is different from the resting state of the patient, the flow calculated with a hyperemic-to-rest flow rate ratio applied to the first flow;

calculating, by the processor, a change in pressure in the blood vessel of the patient, wherein the blood vessel comprises a stenosis;

computing, by the processor, the fractional flow reserve based on the hyperemia flow and the change in pressure; and reporting the fractional flow reserve to assess coronary artery disease in the patient.

9. The computer-implemented method of claim 8 wherein computing the fractional flow reserve comprises computing with computational fluid dynamics using the hyperemic flow calculated from the rest-state flow.

10. A system for computing a hemodynamic quantity, the system comprising:

a processor;

a non-transitory memory coupled to the processor;

first logic stored in the memory and executable by the processor to cause the processor to acquire angiography data from a patient at a resting state of the patient and calculating a first flow in a blood vessel of the patient based on the angiography data, wherein the first flow corresponds to the patient at rest, the first flow comprising rest-state flow;

second logic stored in the memory and executable by the processor to cause the processor to calculate a hyperemia flow by applying a hyperemic-to-rest flow rate ratio to the first flow, wherein the hyperemia flow corresponds to a hyperemic state of the patient that is different from the resting state of the patient;

third logic stored in the memory and executable by the processor to cause the processor to calculate a change in pressure in a blood vessel of the patient based on the angiography data; and fourth logic stored in the memory and executable by the processor to cause the processor to compute the hemodynamic quantity as a fractional flow reserve based on the flow and/or the change in pressure; and a display configured to output the fractional flow reserve to assess coronary artery disease in the patient.

11. The system of claim 10 further comprising fifth logic stored in the memory and executable by the processor to cause the processor to monitor movement of a contrast agent in the blood vessel.

12. The system of claim 10 further comprising fifth logic stored in the memory and executable by the processor to cause the processor to model at least a portion of the blood vessel based on the angiography data.

13. A non-transitory computer readable storage medium having stored therein data representing instructions executable by a programmed processor for computing a hemodynamic quantity, the storage medium comprising instructions for:

acquiring angiography data from a patient at a rest state of the patient;

calculating a first flow in a blood vessel of the patient based on the angiography data, wherein the first flow corresponds to the patient at rest, the first flow comprising rest-state flow calculating a hyperemic flow based on the angiography data, wherein the hyperemic flow corresponds to a hyperemic state of the patient that is different from the rest state of the patient, the hyperemia flow calculated with a hyperemic-to-rest flow rate ratio applied to the first flow;

calculating a change in pressure in a blood vessel of the patient based on the angiography data;

computing the hemodynamic quantity as a fractional flow reserve based on the flow and/or the change in pressure; and using fractional flow reserve to assess coronary artery disease in the patient.

* * * * *